United States Patent [19]

Gregory et al.

[11] Patent Number: 5,292,529
[45] Date of Patent: Mar. 8, 1994

[54] PRESERVED SUNSCREEN COMPOSITION

[75] Inventors: Marion F. Gregory, Bebington; Christine Morris, Upton By Chester, both of United Kingdom

[73] Assignee: Chesebrough-Pond's USA Co., Division of Conopco, Inc., Greenwich, Conn.

[21] Appl. No.: 905,941

[22] Filed: Jun. 29, 1992

[30] Foreign Application Priority Data

Jul. 2, 1991 [GB] United Kingdom ............... 9114317

[51] Int. Cl.$^5$ .................... A61K 7/06; A61K 7/42; A61K 7/44; A61K 7/48
[52] U.S. Cl. ........................... 424/59; 424/60; 424/70; 514/844; 514/847
[58] Field of Search ........................... 424/59

[56] References Cited

U.S. PATENT DOCUMENTS

| | | | |
|---|---|---|---|
| 4,562,067 | 12/1985 | Hopp et al. | 424/59 |
| 4,704,473 | 11/1987 | Nakamura et al. | 562/463 |
| 4,746,738 | 5/1988 | Hanefeld et al. | 544/54 |
| 4,814,162 | 3/1989 | Lang et al. | 514/969 |
| 4,988,501 | 1/1991 | Gosciniak | 424/60 |
| 5,061,480 | 10/1991 | Marchese et al. | 424/59 |
| 5,082,660 | 1/1992 | Ounanian et al. | 424/60 |
| 5,100,656 | 3/1992 | Lang et al. | 424/70 |

FOREIGN PATENT DOCUMENTS

| | | | |
|---|---|---|---|
| 0114607 | 8/1984 | European Pat. Off. | 424/59 |
| 0193387 | 9/1986 | European Pat. Off. | 424/59 |
| 0255157 | 2/1988 | European Pat. Off. | 424/59 |
| 0308543 | 3/1989 | European Pat. Off. | 424/59 |
| 0431755 | 6/1991 | European Pat. Off. | 424/59 |
| 3434885 | 3/1986 | Fed. Rep. of Germany | 424/59 |
| 1553094 | 9/1979 | United Kingdom | 424/59 |
| 2038807 | 7/1980 | United Kingdom | 424/59 |
| 2230186 | 10/1990 | United Kingdom | 424/62 |

OTHER PUBLICATIONS

Sagarin, Cosmetics Science and Technology, 1957, pp. 1048 & 1057-1070.
European Search Report Nov. 20, 1992.

Primary Examiner—Dale R. Ore
Attorney, Agent, or Firm—Milton L. Honig

[57] ABSTRACT

Preserved sunscreen compositions comprising 0.1 to 20% by weight of a substituted 1,3-diketone, a preservative system comprising 0.1 to 5% by weight of an organic acid and a cosmetically acceptable carrier for the sunscreen, the composition having a pH value not exceeding pH 6.

3 Claims, No Drawings

PRESERVED SUNSCREEN COMPOSITION

FIELD OF THE INVENTION

The invention relates to preserved sunscreen compositions, particularly compositions comprising a special UV A-filter and a special organic acid or salt thereof, the compositions having an acid pH and excellent stability during prolonged storage.

BACKGROUND AND PRIOR ART

The sunscreen material, 4-(1,1-dimethylethyl)-4'-methoxydibenzoylmethane, known also as Parsol 1789, is supplied by L. Givaudan & Cie Société, and is described in their GB 2 038 807, as being an outstanding UV A-filter, in that it brings about a considerable retardation in the ageing of the skin with excellent skin tolerance stability (to light, heat and to moisture).

In order to prepare an effective composition to enable a sunscreen material such as this to be applied to the human body surface, particularly to the skin or hair, it is necessary to distribute this sunscreen in a suitable carrier or diluent, at a suitable concentration to facilitate its application at a correct dose over the body surface. The composition so employed must also possess excellent preservative properties, such that the sunscreen material itself does not lose its ability to function as a UV A-filter, and also such that the composition itself is immune from microbial spoilage.

In trade literature issued by Givaudan, the following compatible substances having preservative and antimicrobial compatibility are suggested, (CTFA Designation):

Glutaral
Phenoxyethanol
Chlorhexidine
Propylene Glycol (and)
5-Bromo-5-Nitro-1,3-Dioxane
Methylparaben
Propylparaben
Butylparaben
Triclosan
Methylchloroisothiazolinone (and)
Methylisothiazolinone
Benzalkonium Chloride
Triclocarban We have carried out extensive trials testing the ability of those from this list which are cosmetically acceptable, but have failed to show that any one, or any combination of them, is sufficiently powerful to preserve some sunscreen compositions containing the sunscreen in question against microbial spoilage, particularly against the effects of yeasts and gram-negative bacteria.

We have also examined the effects of some of the so-called compatible preservative and anti-microbial materials identified by Givaudan in their trade literature, including imidazolidinyl urea (also known as Germall 115) and diazolidinyl urea (also known as Germall II) and have confirmed that the UV A-filter activity of the sunscreen PARSOL 1789 is adversely effected.

The invention is accordingly concerned with the discovery that certain other preservative agents that are not only effective in preserving compositions containing this sunscreen against most microbial spoilage organisms, but also totally compatible with it. Furthermore, these other preservative agents have never been proposed for use with it, either by Givaudan in their trade literature nor in any other source.

DEFINITION OF THE INVENTION

Accordingly, the invention provides a preserved sunscreen composition suitable for topical application to the surface of the human body in order to provide a least some protection from the injurious effects of UV A-radiation, which composition comprises:

i) from 0.1 to 20% by weight of a substituted 1,3-diketone having the structure (1):

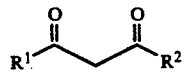

or its tautomer having the structure (2):

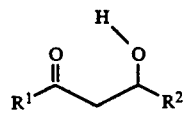

wherein $R^1$ and $R^2$ may be the same or different, and are chosen from benzylidine, substituted benzylidine, phenyl or substituted phenyl groups.

ii) from 0.1 to 5% by weight of an organic acid chosen from sorbic acid, benzoic acid, salicylic acid, propionic acid, dehydroacetic acid, p-hydroxybenzoic acid and alkali metal salts and esters thereof and mixtures thereof; and iii) a cosmetically acceptable carrier for the sunscreen;

the composition having a pH value not exceeding pH 6.

DISCLOSURE OF THE INVENTION

The Substituted 1,3-diketone

The composition according to the invention comprises as a sunscreen a substituted 1,3-diketone in an amount sufficient to provide protection from excessive exposure to ultra-violet rays.

The substituted 1,3-diketone will normally have an absorption band in the region of from 250 to 500 nm, spanning both the UV-A and UV-B ranges, and an extinction coefficient − of from 5,000 to 70,000.

Preferably, the sunscreen has a basic 1,3-diketone chromophore and suitable auxochrome groups providing at least one absorption band in the 280–450 nm region and an extinction coefficient − of from 10,000 to 60,000.

The substituted 1,3-diketone for use as a sunscreen in the composition according to the invention is shown by tautomeric structures (1) and (2):

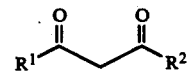

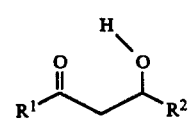

wherein $R^1$ and $R^2$ may be the same or different, and are chosen from benzylidine, substituted benzylidine, phenyl or substituted phenyl groups.

Preferred examples of the groups $R^1$ and $R^2$ are shown in the following structures (3) to (9):

(3) 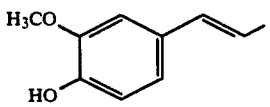

(4) 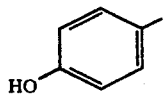

(5) 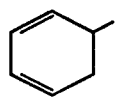

(6) 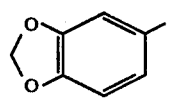

(7) 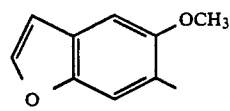

(8) 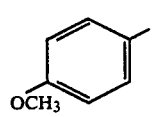

(9) 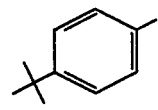

Specific examples of natural compounds for use in the composition of the invention are curcumin, and its analogues demethoxy and didemethoxy curcumin, which can be isolated from *Curcuma longa* roots, and pongamol which can be isolated from *Pongamia glabra* seeds.

Curcumin is also known as di-4-hydroxy-3-methoxy-cinnamoyl methane and has the structure (10):

(10) 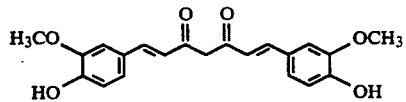

Pongamol is also known as 1,3-propanedione, 1-(4-methoxy-5-benzofuranyl)-3-phenyl and has the structure (11):

(11) 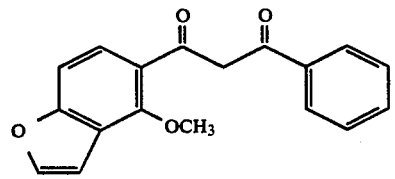

An example of a Synthetic compound for use in the composition according to the invention is the sunscreen, 4-(1,1-dimethylethyl) -4'-methoxydibenzoyl-methane, also known as PARSOL 1789. This sunscreen material absorbs broadly across the UV range enabling retardation in the ageing of skin with excellent skin tolerance and stability, in particular to the effects of light, heat and moisture.

The Preservative

The composition according to the invention also comprises as a preservative an organic acid chosen from sorbic acid, benzoic acid, salicylic acid, propionic acid, dehydroacetic acid, p-hydroxybenoic acid and alkali metal salts and esters thereof, and mixtures thereof.

Examples of suitable alkali metal salts are potassium sorbate, sodium benzoate and sodium salicylate.

Examples of suitable esters are methyl sorbate, ethyl benzoate and ethyl salicylate.

The composition according to the invention comprises from 0.1 to 5%, preferably 0.2 to 4% by weight of the preservative.

The Cosmetically Acceptable Carrier

The composition according to the invention also comprises a cosmetically acceptable vehicle to act as a dilutant, dispersant or carrier for other materials present in the composition, so as to facilitate their distribution when the composition is applied to the skin and/or hair.

Vehicles other than water can include liquid or solid emollients, solvents, humectants, thickeners and powders. Examples of each of these types of vehicle, which can be used singly or as mixtures of one or more vehicles, are as follows:

Emollients, such as stearyl alcohol, glyceryl monoricinoleate, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, olive oil, palm kernel oil, rapeseed oil, safflower seed oil, evening primrose oil, soybean oil, sunflower seed oil, avocado oil, sesame seed oil, coconut oil, arachis oil, castor oil, acetylated lanolin alcohols, petroleum jelly, mineral oil, butyl myristate, isostearic acid, palmitic acid, isopropyl linoleate, lauryl lactate, myristyl lactate, decyl oleate, myristyl myristate;

Propellants, such as propane, butane, isobutane, dimethyl ether, carbon dioxide, nitrous oxide; Solvents, such as ethyl alcohol, methylene chloride, isopropanol, acetone, ethylene glycol monoethyl ether, diethylene glycol monobutyl ether, diethylene glycol monoethyl ether, dimethyl sulphoxide, dimethyl formamide, tetrahydrofuran;

Powders, such as chalk, talc, fullers earth, kaolin, starch, gums, colloidal silica sodium polyacrylate, tetra alkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, ethylene glycol monostearate.

The cosmetically acceptable vehicle will usually form from 10 to 99.9%, preferably from 50 to 99% by weight of the emulsion, and can, in the absence of other cosmetic adjuncts, form the balance of the emulsion.

pH

The composition according to the invention should have a pH value not exceeding pH 6. Preferably, the pH value of the composition is from pH 4 to pH 6, more preferably from pH 5 to pH 5.5.

Adjustment of pH can be achieved by addition of a pH adjustant as conventionally used in the cosmetics art.

Other Sunscreen Materials

The composition according to the invention can also optionally comprise sunscreen materials other than 4,-(1,1-dimethylethyl)-4'-methoxydibenzoyl-methane, preferred amongst which are UV B-filters to provide a wider range of protection against the adverse effects of ultra-violet radiation. These other sunscreens can comprise both organic sunscreens and inorganic sunscreens.

Other Organic Sunscreens

The composition of the invention optionally can comprise one or more other organic sunscreens, in addition to PARSOL 1789, further to enhance the benefit of the composition in providing protection from the harmful effects of excessive exposure to sunlight.

Examples of other suitable organic sunscreens, when required, include those set out in Table 1 below, and mixtures thereof.

TABLE 1

| CTFA Name | Trade Name | Supplier |
|---|---|---|
| Benzophenone-3 | UVINUL M-40 | BASF Chemical Co. |
| Benzophenone-4 | UVINUL MS-40 | BASF Chemical Co. |
| Benzophenone-8 | SPECRA-SORB UV-24 | American Cyanamide |
| DEA Methoxycinnamate | BERNEL HYDRO | Bernel Chemical |
| Ethyl dihydroxypropyl-PABA | AMERSCREEN P | Amerchol Corp. |
| Glyceryl PABA | NIPA G.M.P.A. | Nipa Labs. |
| Homosalate | KEMESTER HMS | Hunko Chemical |
| Methyl anthranilate | SUNAROME UVA | Felton Worldwide |
| Octocrylene | UVINUL N-539 | BASF Chemical Co. |
| Octyl dimethyl PABA | AMERSCOL | Amerchol Corp. |
| Octyl methoxycinnamate | PARSOL MCX | Givaudan |
| Octyl salicylate | SUNAROME WMO | Felton Worldwide |
| PABA | PABA | National Starch |
| 2-Phenyl-benzimidazole-5-sulphonic acid | EUSOLEX 232 | EM Industries |
| TEA salicylate | SUNAROME W | Felton Worldwide |
| 3-(4-methylbenzylidene)-camphor | EUSOLEX 6300 | EM Industries |
| Benzophenone-1 | UVINUL 400 | BASF Chemical Co. |
| Benzophenone-2 | UVINUL D-50 | BASF Chemical Co. |
| Benzophenone-6 | UVINUL D-49 | BASF Chemical Co. |
| Benzophenone-12 | UVINUL 408 | BASF Chemical Co. |
| 4-Isopropyl dibenzoyl methane | EUSOLEX 8020 | EM Industries |
| Etocrylene | UVINUL N-35 | BASF Chemical Co. |

The composition of the invention can accordingly comprise from 0.1 to 20%, preferably from 1 to 10% by weight of other organic sunscreen material.

Inorganic Sunscreens

The composition of the invention optionally can also comprise one or more inorganic sunscreens.

Currently, the most widely used inorganic sunscreen is ultrafine titanium dioxide, having an average particle size of from 1 to 100 nm, preferably from 10 to 40 nm, which offers both absorbance and reflectance of ultra violet light. This sunscreen is compatible with pongamol, curcumin and PARSOL 1789, and with other substituted 1,3-diketones as herein defined.

Examples of other inorganic sunscreens include zinc oxide, iron oxide, silica, such as fumed silica and boron nitride, each having an average particle size of from 1 to 100 nm.

Optional Skin Benefit Materials and Cosmetic Adjuncts

A particularly convenient form of the composition according to the invention is an emulsion, in which case an oil or oily material will normally be present, together with an emulsifier to provide either a water-in-oil emulsion or an oil-in-water emulsion, depending largely on the average hydrophilic-lyophilic balance (HLB) of the emulsifier employed.

Oil or Oily Material

The composition according to the invention can optionally comprise one or more oils or other materials having the properties of an oil.

Examples of suitable oils include mineral oil and vegetable oils, and oil materials, such as those already proposed herein as emollients. Other oils or oily materials include silicone oils, both volatile and non-volatile, such as polydimethyl siloxanes.

The oil or oily material, when present for the purposes for forming an emulsion, will normally form up to 90%, preferably from 10 to 80% by volume of the composition.

Emulsifier

The composition according to the invention can also optionally comprise one or more emulsifiers the choice of which will normally determine whether a water-in-oil or and oil-in-water emulsion is formed.

When a water-in-oil emulsion is required, the chosen emulsifier or emulsifiers should normally have an average HLB value of from 1 to 6. When an oil-in-water emulsion is required, a chosen emulsifier or emulsifiers should have an average HLB value of >6.

Examples of suitable emulsifiers are set below in Table 2 in which the chemical name of the emulsifiers is given together with an example of a trade name as commercially available, and the average HLB value.

TABLE 2

| Chemical Name of Emulsifier | Trade Name | HLB Value |
|---|---|---|
| Sorbitan trioleate | Arlacel 85 | 1.8 |
| Sorbitan tristearate | Span 65 | 2.1 |
| Glycerol monooleate | Aldo MD | 2.7 |
| Glycerol monostearate | Atmul 84S | 2.8 |
| Glycerol monolaurate | Aldo MC | 3.3 |
| Sorbitan sesquioleate | Arlacel 83 | 3.7 |
| Sorbitan monooleate | Arlacel 80 | 4.3 |
| Sorbitan monostearate | Span 60 | 4.7 |
| Poloxyethylene (2) stearyl ether | Brij 72 | 4.9 |
| Poloxyethylene sorbitol beeswax derivative | G-1702 | 5 |
| PEG 200 dilaurate | Emerest 2622 | 6.3 |
| Sorbitan monopalmitate | Arlacel 40 | 6.7 |
| Polyoxyethylene (3.5) nonyl phenol | Emulgen 903 | 7.8 |
| PEG 200 monostearate | Tegester PEG 200 MS | 8.5 |
| Sorbitan monolaurate | Arlacel 200 | 8.6 |
| PEG 400 dioleate | Tegester PEG | 8.8 |

TABLE 2-continued

| Chemical Name of Emulsifier | Trade Name | HLB Value |
|---|---|---|
| | 400-DO | |
| Polyoxyethylene (5) monostearate | Ethofat 60-16 | 9.0 |
| Polyoxyethylene (4) sorbitan monostearate | Tween 61 | 9.6 |
| Polyoxyethylene (4) lauryl ether | Brij 30 | 9.7 |
| Polyoxyethylene (5) sorbitan monooleate | Tween 81 | 10.0 |
| PEG 300 monooleate | Neutronyx 834 | 10.4 |
| Polyoxyethylene (20) sorbitan tristearate | Tween 65 | 10.5 |
| Polyoxyethylene (20) sorbitan trioleate | Tween 85 | 11.0 |
| Polyoxyethylene (8) monostearate | Myrj 45 | 11.1 |
| PEG 400 monooleate | Emerest 2646 | 11.7 |
| PEG 400 monostearate | Tegester PEG 400 | 11.9 |
| Polyoxyethylene 10 monooleate | Ethofat 0/20 | 12.2 |
| Polyoxyethylene (10) stearyl ether | Brij 76 | 12.4 |
| Polyoxyethylene (10) cetyl ether | Brij 56 | 12.9 |
| Polyoxyethylene (9.3) octyl phenol | Triton X-100 | 13.0 |
| Polyoxyethylene (4) sorbitan monolaurate | Tween 21 | 13.3 |
| PEG 600 monooleate | Emerest 2660 | 13.7 |
| PEG 1000 dilaurate | Kessco | 13.9 |
| Polyoxyethylene sorbitol lanolin derivative | G-1441 | 14.0 |
| Polyoxyethylene (12) lauryl ether | Ethosperse LA-12 | 14.4 |
| PEG 1500 dioleate | Pegosperse 1500 | 14.6 |
| Polyoxyethylene (14) laurate | Arosurf HFL-714 | 14.8 |
| Polyoxyethylene (20) sorbitan monostearate | Tween 60 | 14.9 |
| Polyoxyethylene 20 sorbitan monooleate | Tween 80 | 15.0 |
| Polyoxyethylene (20) stearate | Myrj 49 | 15.0 |
| Polyoxyethylene (20) stearyl ether | Brij 78 | 15.3 |
| Polyoxyethylene (20) sorbitan monopalmitate | Tween 40 | 15.6 |
| Polyoxyethylene (20) cetyl ether | Brij 58 | 15.7 |
| Polyoxyethylene (25) oxypropylene monostearate | G-2162 | 16.0 |
| Polyoxyethylene (20) sorbitol monolaurate | Tween 20 | 16.7 |
| Polyoxyethylene (23) lauryl ether | Brij 35 | 16.9 |
| Polyoxyethylene (50) monostearate | Myrj 53 | 17.9 |
| PEG 4000 monostearate | Pegosperse 4000 MS | 18.7 |

The foregoing list of emulsifiers is not intended to be limiting and merely exemplifies selected emulsifiers which are suitable for use in accordance with the invention.

It is to be understood that two or more emulsifiers can be employed if desired.

The amount of emulsifier or mixtures thereof, to be incorporated in the composition of the invention, when appropriate is from 1 to 50%, preferably from 2 to 20% and most preferably from 2 to 10% by weight of the composition.

Water

The composition of the invention can also comprise water, usually up to 80%, preferably from 5 to 80% by volume.

Silicone Surfactant

The composition of the invention can also optionally comprise a high molecular weight silicone surfactant which can also act as an emulsifier, in place of or in addition to the optional emulsifier(s) already mentioned.

The silicone surfactant is a high molecular weight polymer of dimethyl polysiloxane with polyoxyethylene and/or polyoxypropylene side chains having a molecular weight of from 10,000 to 50,000 and having the structure:

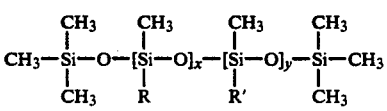

where
R is a $C_{1-18}$ alkyl group and
R' is a polyether group having the structure:

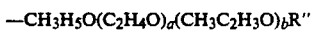

where R" is H or a $C_{1-18}$ alkyl group,
a has a value of from 9 to 115,
b has a value of from 0 to 50,
x has a value of from 133 to 673,
y has a value of from 25 to 0.25.

Preferably, the dimethyl polysiloxane polymer is one in which:
a has a value of from 10 to 114
b has a value of from 0 to 49
x has a value of from 388 to 402
y has a value of from 15 to 0.75
one of groups R' and R" being lauryl, and the other having a molecular weight of from 1000 to 5000.

A particularly preferred dimethyl polysiloxane polymer is one in which:
a has the value 14
b has the value 13
x has the value 249
y has the value 1.25

The dimethyl polysiloxane polymer is conveniently provided as a dispersion in a volatile siloxane, the dispersion comprising, for example, from 1 to 20% by volume of the polymer and from 80 to 99% by volume of the volatile siloxane. Ideally, the dispersion consists of a 10% by volume of the polymer dispersed in the volatile siloxane.

Examples of the volatile siloxanes in which the polysiloxane polymer can be dispersed include polydimethyl siloxane (pentamer and/or hexamer).

A particularly preferred silicone surfactant is cyclomethicone and dimethicone copolyol, such as DC 3225C Formulation Aid available from DOW CORNING. Another is laurylmethicone copolyol, such as DC Q2-5200, also available from Dow Corning.

The amount of silicone surfactant, when present in the composition will normally be up to 25%, preferably from 0.5 to 15% by weight of the emulsion.

Surfactant

The composition according to the invention can also optionally comprise a surfactant chosen from anionic, nonionic or amphoteric surfactant or mixtures thereof, particularly when the composition is intended to wash hair or skin.

Suitable anionic surfactants for this purpose are the alkyl sulphates, alkyl ether sulphates, alkaryl sulphonates, alkyl succinates, alkyl sulphosuccinates, N-alkoyl sarcosinates, alkyl carboxylates, alkanyl isethionates, alkoyl taurates, alkyl phosphates, and alpha-olefin sulphonates, especially their sodium, magnesium, ammonium and mono-, di- and triethanolamine salts. The alkyl groups generally contain from 8 to 18 carbon atoms and may be unsaturated. The alkyl ether sulphates may contain from one to 10 ethylene oxide or propylene oxide units per molecule, and preferably contain 2 to 3 ethylene oxide units per molecule.

The nonionic surfactants suitable for optional use in the composition of the invention may include condensation products of aliphatic ($C_8$–$C_{18}$) primary or secondary linear or branched chain alcohols or alkanolic acids or phenols with alkylene oxides, usually ethylene oxide and generally 6–30 EO.

Other suitable nonionics include mono or di alkyl alkanolamides or alkyl polyglucosides. Examples include coco mono or diethanolamide, coco mono isopropanolamide, and coco di glucoside.

The amphoteric surfactants suitable for optional use in the composition of the invention may include alkyl betaines, alkyl amidopropyl betaines, alkyl sulphobetaines, alkoyl amphoglycinates, wherein the alkyl groups have from 8 to 18 carbon atoms. Examples include cocomidopropyl betaine, cocodimethyl sulphopropyl betaine and preferably cocobetaine.

The surfactants when present in the composition of the invention form from 2 to 40% by weight, and preferably from 5 to 30% by weight.

Other Cosmetic Adjuncts

Examples of conventional adjuncts which can optionally be employed include antioxidants, such butyl hydroxy toluene; humectants, such as glycerol, sorbitol, 2-pyrrolidone-5-carboxylate, dibutylphthalate, gelatin, polyethylene glycol, such as PEG 200-600; buffers, such as lactic acid together with a base such as triethanolamine or sodium hydroxide; waxes, such as beeswax, ozokerite wax, paraffin wax: plant extracts, such as Aloe vera, cornflower, witch hazel, elderflower, cucumber; thickeners; activity enhancers; colourants; and perfumes. Cosmetic adjuncts can form the balance of the composition.

Use of the Composition

The composition according to the invention is intended primarily as a sun care product for topical application to human skin to protect exposed skin from the harmful effects of excessive exposure to sunlight.

In use, a small quantity of the composition, for example from 1 to 5 ml, is applied to exposed areas of the skin or hair, from a suitable container or applicator and, if necessary, it is then spread over and/or rubbed into the skin using the hand or fingers or a suitable device, or applied as a shampoo or conditioner.

Product Form and Packaging

The topical skin and/or hair treatment composition of the invention can be formulated as a liquid or gel, a shampoo or hair conditioner, or as a lotion having a viscosity of from 4,000 to 10,000 mPas, a fluid cream having a viscosity of from 10,000 to 20,000 mPas or a cream having a viscosity of from 20,000 to 100,000 mPas, or above. The composition can be packaged in a suitable container to suit its viscosity and intended use by the consumer.

For example, a liquid, gel, lotion or fluid cream can be packaged in a bottle or a roll-ball applicator or a propellant-driven aerosol device or a container fitted with a pump suitable for finger operation. As a shampoo or hair conditioner, this composition can be packaged in a bottle or sachet. When the composition is a cream, it can simply be stored in a non-deformable bottle or squeeze container, such as a tube or a lidded jar.

The invention accordingly also provides a closed container containing a cosmetically acceptable composition as herein defined.

Process

The invention also provides a process for preparing a preserved sunscreen composition which comprise the steps of distributing an effective amount of a sunscreen chosen from substituted 1,3-diketones, as herein defined, together with an effective amount of a preservative chosen from organic acid or their derivatives, as herein defined, in a cosmetically acceptable carrier for the sunscreen, and adjusting the pH of the composition so formed, as necessary, to a value not exceeding pH 6.

EXAMPLES

The invention is illustrated by the following examples.

Examples 1 and 2: Comparative Examples a, b and c

Challenge Test Procedure for evaluating antimicrobial activity of preservatives in products containing PARSOL 1789

A test was devised to assess the ability of selected substances to preserve, against microbial spoilage, sunscreen compositions containing PARSOL 1789, both those compositions according to the invention (Examples 1 and 2) and, by way of comparison, others containing different preservative substances as recommended by Givaudan (Comparative Examples a, b and c).

This test involved incubating under standard conditions test compositions which have been inoculated with a selected bacterium, yeast or a mixture of moulds. Each test composition was repeatedly inoculated at regular intervals ("challenged"), until the surviving microorganisms from the inoculation showed an increase above a standard level, at which point, the preservative systems under test was judged to have failed. Accordingly, the higher the number of "challenges", the better is the preservative substance in preventing or at least delaying microbial spoilage.

Materials

Preservative Materials

Example 1—Sorbic acid, methyl paraben, propyl paraben and phenoxyethanol

Example 2—potassium sorbate, methyl paraben, propyl paraben and phenoxyethanol

Comparative Example a—no preservative
Comparative Example b—methyl paraben, propyl paraben
Comparative Example c—methyl paraben, propyl paraben and phenoxyethanol The micro-organisms selected for this test were:
i) *Pseudomonas cepacia*—a gram-negative bacterium,
ii) *Candida parapsilosis*—a yeast, and
iii) *Aspergillus niger* & Penicillium sp.,—a mixture of moulds The formulation used in the Challenge Test was an emulsion (cream) containing the following ingredients:

|  | % w/w |
|---|---|
| Parsol 1789 | 2 |
| Iso-propyl myristate | 10 |
| Stearic acid | 1 |
| Potassium cetyl phosphate | 1 |
| Carboxyvinyl polymer (Carbopol 940) | 0.3 |
| Magnesium aluminium stearate (Veegum) | 0.15 |
| "Preservative" | qs* |
| Water | to 100 |

*the mixture of preservative agents as set out in Table 3 for Examples 1 and 2 and Comparative Examples a-c (see infra).

In each case the pH value of the formulations was adjusted to 5.3.

Method

The method of testing was as follows:
i) Introduce aseptically 99 ml of test composition into a 250 ml flask and add 1 ml of inoculum of one of the test organisms (see above), to provide a dilution of $10^6$ cells/ml in the composition.
ii) mix and incubate at 28° C. for 24 hours.
iii) remove 1 ml of incubated composition from the flask and add to it 9 ml of peptone water/Tween 80 as diluent and mix thoroughly.
iv) place 1 ml of diluted sample into a petri dish and add warm, molten agar (40° C.) and mix to distribute culture uniformly and allow to set.
v) incubate plates for 3 days at 28° C. and then count colonies and note log reduction of count (due to the presence of the preservative in the original culture composition).

The inoculation of the organisms originally introduced into each composition is then repeated at 24 hour intervals, following removal of the first total viable count sample, the plating out and counting procedure being repeated on each occasion. The test is terminated when the samples show a contamination level greater than $10^2$ counts per ml on 2 consecutive days. This point is regarded as the failure point for the composition under test.

The greater the number of inoculations of contaminant organisms before this level of contamination is established in the composition, the better the preservative system.

The above procedure applies to the inoculation of the bacterium and the yeast, and this procedure was varied slightly with the mixed culture of moulds as follows:
i) two samples of each test composition (9.9 ml and 9 ml) were transferred to sterile flasks and 0.1 ml or 1 ml of a mould spore suspension (approximately $10^8$ spores per ml) was introduced into the respective samples and thoroughly mixed. The inoculated samples were incubated at 28° C. for up to 28 days with 1 ml samples being aseptically removed for the total viable count as outlined above using Sabouraud's dextrose agar after 1, 7, and 28 days.
ii) "Low risk" compositions eliminate mould spores in 1 to 2 days, "medium risk" compositions take 7 to 14 days to eliminate the spores and the "high risk" compositions still have surviving mould spores after 14 days incubation.

Results

Table 3 below summarises the results obtained. These results indicate the good preservation which can be obtained with test formulations containing a sorbate or sorbic acid preservative, in contrast with the control formulations containing 2 or 3 preservatives recommended by Givaudan, where the Bacterial Challenge Test failed in 1 day and the Mould Challenge Test indicated that mould spores survived and proliferated beyond 1 day.

TABLE 3

| Example | Methyl paraben | Propyl paraben | Phenoxy-ethanol | Sorbic acid | Potassium sorbate | Bacterial challenges to failure | Mould 1% | Mould 10% |
|---|---|---|---|---|---|---|---|---|
| 1 | 0.3 | 0.15 | 0.4 | 0.5 | — | >21 | — | — |
| 2 | 0.2 | 0.1 | 0.4 | — | 0.5 | >21 | — | — |
| A | — | — | — | — | — | 1 | ++++ | ++++ |
| B | 0.2 | 0.1 | — | — | — | 1 | + | +++ |
| C | 0.2 | 0.1 | 0.4 | — | — | 1 | + | +++ |

Key to mould challenge:
— No mould survival after 1 day
+ Mould survival on day 1, no survival on days 7, 14 or 28
++ Mould survival on days 1, 7; no survival on days 14, 28
+++ Mould survival on days 1, 7, 14; no survival on day 28
++++ Mould survival on days 1, 7, 14 & 28

Rapid Challenge Test Procedure for evaluating antimicrobial activity of preservatives in products containing Parsol 1789

EXAMPLES 3-6: COMPARATIVE EXAMPLES d - i

With the repeat challenge test inoculations are made daily until the organisms establish themselves in the product. This inoculation (1 ml daily) in effect dilutes the product over the 20+ days of the test. The rapid challenge involves diluting the product on day 1, adding organisms and assessing the preservative capacity of the diluted product at 24 hours and 7 days.

The following dilutions are used:

| CODE | PRODUCT | WATER | INOCULUM |
|---|---|---|---|
| A | 9.9 g | — | 0.1 ml |
| C | 9.0 g | 0.9 | 0.1 ml |
| E | 8.0 g | 1.9 | 0.1 ml |
| G | 7.0 g | 2.9 | 0.1 ml |
| I | 6.0 g | 3.9 | 0.1 ml |

The level of inoculum is such that initially the count in the product will be $10^6 g^{-1}$. Total viable counts are carried out after 24 hours and 7 days using the method previously described for the repeat challenge test.

If the organisms establish themselves in dilution A after 24 hours and 7 days this indicates a highly susceptible product with a failure rate equivalent to 1 inoculation in the repeat challenge test described for Example 1.

Failure at A = Failure at 1 inoculation in repeat test
Failure at C = Failure at 5 inoculations in repeat test
Failure at E = Failure at 10 inoculations in repeat test
Failure at G = Failure at 15 inoculations in repeat test
Failure at I = Failure at 20+ inoculations in repeat test A series of compositions containing Parsol 1789 was prepared for testing, each containing preservative materials chosen from those in accordance with the invention (Examples 3 and 4) and others containing preservative substances as recommended by Givaudan (Comparative Examples d - i). Each composition was tested at two different pH values to show the effect of pH on the preservative system.

Materials

|  | % w/w |
| --- | --- |
| Mono, di, tri-($C_{12}$-$C_{14}$ tetraglycol ether)-O-phosphonic acid esters | 9 |
| Paraffin oil | 30 |
| Isopropylpalmitate | 6 |
| Silicone oil (20 CTS) | 1 |
| Lanolin oil | 1 |
| Cetyl alcohol | 2 |
| Parsol 1789 | 2 |
| Ultrafine $TiO_2$ | 2 |
| "preservative" | qs* |
| Perfume | qs |
| Colour | qs |
| Water | to 100 |

*the mixture of preservative agents as set out in Table 4 for Examples 3-6 and Comparative Examples d-i (see infra).

In each case the pH value of the formulation was adjusted to the values shown in Table 4.

Results

Results are shown in Table 4.

Only samples comprising potassium sorbate at a pH of less than 6.0 are well preserved against yeasts, moulds and bacteria.

The failure point for the samples inoculated with bacteria or yeast was equivalent to 20+ inoculations in a repeat challenge test.

Key to mould challenge:
— = no survival at 24 hours and 7 days
+++ = moderate level of survival at 24 hours and 7 days
++++ = high level of survival of mould spores at 24 hours and 7 days

TABLE 4

| | | PRESERVATIVE | | | | FAILURE POINT | | | |
| | | Methyl | Propyl | Phenoxy- | Potassium | | | Mould | |
| EXAMPLE | pH | paraben | paraben | ethanol | sorbate | Bacteria | Yeast | 1% | 10% |
| --- | --- | --- | --- | --- | --- | --- | --- | --- | --- |
| 3 | 7.54 | — | — | — | 0.5 | I | A | ++++ | ++++ |
| 4 | 5.5 | — | — | — | 0.5 | I | I | — | — |
| 5 | 7.51 | 0.2 | 0.1 | — | 0.5 | I | E | +++ | +++ |
| 6 | 5.2 | 0.2 | 0.1 | — | 0.5 | I | I | — | — |
| d | 7.62 | — | — | — | — | A | A | ++++ | ++++ |
| e | 5.26 | — | — | — | — | A | A | ++++ | +++ |
| f | 7.55 | 0.2 | 0.1 | — | — | A | A | ++++ | ++++ |
| g | 5.21 | 0.2 | 0.1 | — | — | A | A | ++++ | ++++ |
| h | 7.66 | 0.2 | 0.1 | 0.4 | — | A | A | ++++ | ++++ |
| i | 5.20 | 0.2 | 0.1 | 0.4 | — | A | A | ++++ | ++++ |

Examples 3,4—potassium sorbate
Examples 5,6—potassium sorbate, propyl paraben, methyl paraben
Comparative Examples d, e—no preservative
Comparative Examples f, g—propyl paraben, methyl paraben
Comparative Examples h, i—propyl paraben, methyl paraben, phenoxyethanol The microorganisms selected for the rapid challenge test were:
(i) *Pseudomonas cepecia*; and
(ii) *Candida parapsilosis*

The mould challenge test was carried out using *Aspergillus niger* and *Penicillium Sp* with the standard test as described for Example 1.

The formulation used in these tests was a cream containing the following ingredients:

EXAMPLES 7-9, COMPARATIVE EXAMPLES j - o

The rapid challenge test described above for Example 3 was repeated using a shampoo formulation as follows:

Materials

Example 7, 8—potassium sorbate
Examples 9—potassium sorbate, propyl paraben, methyl paraben
Comparative Examples j, k—No preservative
Comparative Examples l, m—propyl paraben, methyl paraben
Comparative Examples n, o—propyl paraben, methyl paraben, phenoxyethanol The shampoo formulations were tested with a mixture of *Pseudomonas cepacia* and *Klebsiella pneumoniae* bacteria. The formulation used in these tests was a shampoo containing the following ingredients:

|  | % w/w |
| --- | --- |
| Sodium lauryl ether sulphate (2EO) | 12.0 |
| Cocoamidopropylbetaine | 2.0 |
| Guar hydroxypropyltrimonium chloride | 0.1 |
| Parsol 1789 | 0.4 |
| Parsol MCX | 1.5 |
| "preservative" | qs* |
| Perfume | qs |

-continued

| | % w/w |
|---|---|
| Colour | qs |
| Water | to 100 |

*the mixture of preservative agents as et out in Table 5 for Examples 7-9 and Comparative Examples j-o (see infra).

In each case the pH value of the formulation was adjusted to the values shown in Table 5.

Results

Results are shown in Table 5. The failure point for these samples was equivalent to 20+ inoculations in a repeat challenge test.

TABLE 5

| | | PRESERVATIVE | | | | |
|---|---|---|---|---|---|---|
| EXAMPLE | pH | Methyl paraben | Propyl paraben | Phenoxy- ethanol | Potassium sorbate | FAILURE POINT |
| 7 | 6.96 | — | — | — | 0.5 | G |
| 8 | 5.26 | — | — | — | 0.5 | I |
| 9 | 5.29 | 0.2 | 0.1 | — | 0.5 | I |
| j | 6.96 | — | — | — | — | A |
| k | 5.28 | — | — | — | — | A |
| l | 6.92 | 0.2 | 0.1 | — | — | A |
| m | 5.2 | 0.2 | 0.1 | — | — | A |
| n | 6.79 | 0.2 | 0.1 | 0.4 | — | E |
| o | 5.24 | 0.2 | 0.1 | 0.4 | — | B |

The invention is further illustrated by the following examples; in each case, the pH value was adjusted to 5-5.5.

Examples 10 to 14 illustrate cream compositions according to the invention.

EXAMPLE 10

| | % w/w |
|---|---|
| Silicone oil 200 cts | 7.5 |
| Glycerylmonostearate | 3 |
| Cetosteryl alcohol | 1.6 |
| Polyoxyethylene-(20)-cetyl alcohol | 1.4 |
| Xanthan gum | 0.5 |
| Parsol 1789 | 1.5 |
| Octyl methoxycinnate (PARSOL MCX) | 7.0 |
| Potassium sorbate | 0.5 |
| Methylparabens | 0.2 |
| Propylparabens | 0.1 |
| Perfume | qs |
| Colour | qs |
| Water | to 100.00 |

EXAMPLE 11

| | % w/w |
|---|---|
| Decyloleate | 6 |
| Isopropylpalmitate | 6 |
| Polyoxyethylene-(20)-stearate | 0.85 |
| Sorbitan monostearate | 0.6 |
| Triethanolamine | 0.26 |
| Fatty acid esters | 0.2 |
| Carboxyvinylpolymer | 0.26 |
| Methylparabens | 0.2 |
| Propylparabens | 0.2 |
| Parsol 1789 | 2.0 |
| 2-phenyl-benzimidazole-5-sulphonic acid | 4.0 |
| sodium benzoate | 0.5 |
| Perfume | qs |
| Colour | qs |
| Water | to 100 |

EXAMPLE 12

| | % w/w |
|---|---|
| POE*-(2)-stearyl alcohol | 4.8 |
| POE-(20)-stearyl alcohol | 1.2 |
| POP*-(15)-stearyl alcohol | 12.0 |
| Parsol 1789 | 3.0 |
| Parsol MCX | 6.0 |
| Octyl salicylate | 2.0 |
| Methylparabens | 0.2 |
| Propylparabens | 0.2 |
| Benzoic acid | 0.8 |
| Perfume | qs |
| Colour | qs |
| Water | to 100 |

*POE = polyoxyethylene
**POP = polyoxypropylene

EXAMPLE 13

| | % w/w |
|---|---|
| Silicone oil 200 cts | 7.5 |
| Glycerylmonostearate | 3 |
| Cetosteryl alcohol | 1.6 |
| Polyoxyethylene-(20)-cetyl alcohol | 1.4 |
| Xanthan gum | 0.5 |
| Pongamol | 1.5 |
| PARSOL MCX | 7.0 |
| Potassium sorbate | 0.5 |
| Methylparabens | 0.2 |
| Propylparabens | 0.1 |
| Perfume | qs |
| Colour | qs |
| Water | to 100.00 |

EXAMPLE 14

| | % w/w |
|---|---|
| Decyloleate | 6 |
| Isopropylpalmitate | 6 |
| Polyoxyethylene-(20)-stearate | 0.85 |
| Sorbitan monostearate | 0.6 |
| Triethanolamine | 0.26 |
| Fatty acid esters | 0.2 |
| Carboxyvinylpolymer | 0.26 |
| Methylparabens | 0.2 |
| Propylparabens | 0.2 |
| Curcumin | 2.0 |
| 2-phenyl-benzimidazole-5-sulphonic acid | 4.0 |
| Sodium benzoate | 0.5 |
| Perfume | qs |
| Colour | qs |
| Water | to 100 |

Examples 15 to 19 illustrate shampoo compositions according to the invention.

EXAMPLE 15

|  | % w/w |
|---|---|
| Ammonium lauryl sulphate | 14 |
| Ammonium lauryl ether sulphate (2EO) | 4 |
| Coconut monoethanolamide | 1 |
| Parsol 1789 | 1 |
| Octylmethoxycinnamate | 2 |
| Salicylic acid | 0.5 |
| Colour | qs |
| Perfume | qs |
| Water | to 100 |

EXAMPLE 16

|  | % w/w |
|---|---|
| Sodium lauryl ether sulphate (2EO) | 16 |
| Cocoamidopropylbetaine | 2.0 |
| Guar hydroxypropyltrimonium chloride | 0.1 |
| Dimethicone | 1.0 |
| Parsol 1789 | 2 |
| TiO$_2$ (ultra fine) | 0.5 |
| Polyacrylic acid (cross-linked) | 0.4 |
| Benzoic acid | 0.8 |
| Colour | qs |
| Perfume | qs |
| Water | to 100 |

EXAMPLE 17

|  | % w/w |
|---|---|
| Sodium lauryl ether sulphate (2EO) | 12 |
| Cocoamidopropylbetaine | 2 |
| Guar hydroxypropyltrimonium chloride | 0.1 |
| Parsol 1789 | 0.4 |
| Parsol MCX | 1.5 |
| Oxybenzone | 1.0 |
| Potassium sorbate | 0.5 |
| Methylparabens | 0.2 |
| Propylparabens | 0.2 |
| Perfume | qs |
| Colour | qs |
| Water | to 100 |

EXAMPLE 18

|  | % w/w |
|---|---|
| Ammonium lauryl sulphate | 14 |
| Ammonium lauryl ether sulphate (2EO) | 4 |
| Coconut monoethanolamide | 1 |
| Pongamol | 0.5 |
| Octylmethoxycinnamate | 2 |
| Salicylic acid | 1 |
| Colour | qs |
| Perfume | qs |
| Water | to 100 |

EXAMPLE 19

|  | % w/w |
|---|---|
| Sodium lauryl ether sulphate (2EO) | 16.0 |
| Cocoamidopropylbetaine | 2.0 |
| Guar Hydroxypropyltrimonium chloride | 0.1 |
| Dimethicone | 1.0 |
| Curcumin | 1 |
| Benzoic acid | 0.6 |
| Colour | qs |
| Perfume | qs |

-continued

|  | % w/w |
|---|---|
| Water | to 100 |

Examples 20 to 23 illustrate hair conditioner compositions according to the invention.

EXAMPLE 20

|  | % w/w |
|---|---|
| Cetyltrimethylammonium chloride | 1.0 |
| C$_{16-18}$ fatty alcohol | 2.4 |
| Paraffin wax | 1.0 |
| Glyceryl monostearate | 1.0 |
| Parsol 1789 | 0.5 |
| Octylmethoxycinnamate | 2.0 |
| Sorbic acid | 0.5 |
| Methyl parabens | 0.2 |
| Propyl parabens | 0.05 |
| Perfume + colour | qs |
| Water | to 100 |

EXAMPLE 21

|  | % w/w |
|---|---|
| Cetyltrimethyl ammonium chloride | 0.7 |
| C$_{16-18}$ fatty alcohol | 2.0 |
| Hydroxyethyl cellulose (Natrosol 250 HR) | 1.0 |
| Stearyl stearate | 0.5 |
| Parsol 1789 | 1.2 |
| TiO$_2$ (ultra fine) | 0.5 |
| Sodium benzoate | 0.5 |
| Perfume, colour | qs |
| Water | to 100 |

EXAMPLE 22

|  | % w/w |
|---|---|
| Cetyltrimethylammonium chloride | 1.0 |
| C$_{16-18}$ fatty alcohol | 2.4 |
| Paraffin wax | 1.0 |
| Glyceryl monostearate | 1.0 |
| Pongamol | 0.5 |
| Parsol MCX | 1.0 |
| Sorbic acid | 0.5 |
| Methyl parabens | 0.2 |
| Perfume + colour | qs |
| Water | to 100 |

EXAMPLE 23

|  | % w/w |
|---|---|
| Cetyltrimethyl ammonium chloride | 1.1 |
| C$_{16-18}$ fatty alcohol | 2.5 |
| Hydroxyethyl cellulose (Natrosol 250 HR) | 0.8 |
| Stearyl stearate | 0.5 |
| Curcumin | 0.5 |
| Octylmethoxycinnamate | 2.0 |
| Dimethicone | 1.0 |
| Sodium salicylate | 0.5 |
| Perfume, colour | qs |
| Water | to 100 |

We claim:
1. A preserved sunscreen composition suitable for topical application to the surface of the human body, in order to prevent it from the injurious effects of UV A-radiation, which comprises:
  (i) from 0.1 to 20% by weight of 4-(1,1-dimethylethyl)-4'-methoxydibenzoylmethane;
  (ii) from 0.1 to 5% by weight of an organic acid or salt thereof selected from the group consisting of sorbic acid, potassium sorbate and combinations thereof; and
  (iii) a cosmetically acceptable carrier for the sunscreen; the composition having a pH value not exceeding about pH 6.

2. A composition according to claim 1 wherein the pH value of the composition is from pH 4 to pH 6.

3. A composition according to claim 1 wherein the pH value of the composition is from pH 5 to pH 5.5.

* * * * *

UNITED STATES PATENT AND TRADEMARK OFFICE
CERTIFICATE OF CORRECTION

PATENT NO. : 5,292,529

DATED : March 8, 1994

INVENTOR(S) : Gregory, et al

It is certified that error appears in the above-indentified patent and that said Letters Patent is hereby corrected as shown below:

Columns 17 and 18 should be added as per attached sheet.

Signed and Sealed this

Fourth Day of April, 1995

Attest:

BRUCE LEHMAN

Attesting Officer     Commissioner of Patents and Trademarks

EXAMPLE 15

|  | % w/w |
|---|---|
| Ammonium lauryl sulphate | 14 |
| Ammonium lauryl ether sulphate (2EO) | 4 |
| Coconut monoethanolamide | 1 |
| Parsol 1789 | 1 |
| Octylmethoxycinnamate | 2 |
| Salicylic acid | 0.5 |
| Colour | qs |
| Perfume | qs |
| Water | to 100 |

EXAMPLE 16

|  | % w/w |
|---|---|
| Sodium lauryl ether sulphate (2EO) | 16 |
| Cocoamidopropylbetaine | 2.0 |
| Guar hydroxypropyltrimonium chloride | 0.1 |
| Dimethicone | 1.0 |
| Parsol 1789 | 2 |
| $TiO_2$ (ultra fine) | 0.5 |
| Polyacrylic acid (cross-linked) | 0.4 |
| Benzoic acid | 0.8 |
| Colour | qs |
| Perfume | qs |
| Water | to 100 |

EXAMPLE 17

|  | % w/w |
|---|---|
| Sodium lauryl ether sulphate (2EO) | 12 |
| Cocoamidopropylbetaine | 2 |
| Guar hydroxypropyltrimonium chloride | 0.1 |
| Parsol 1789 | 0.4 |
| Parsol MCX | 1.5 |
| Oxybenzone | 1.0 |
| Potassium sorbate | 0.5 |
| Methylparabens | 0.2 |
| Propylparabens | 0.2 |
| Perfume | qs |
| Colour | qs |
| Water | to 100 |

EXAMPLE 18

|  | % w/w |
|---|---|
| Ammonium lauryl sulphate | 14 |
| Ammonium lauryl ether sulphate (2EO) | 4 |
| Coconut monoethanolamide | 1 |
| Pongamol | 0.5 |
| Octylmethoxycinnamate | 2 |
| Salicylic acid | 1 |
| Colour | qs |
| Perfume | qs |
| Water | to 100 |

EXAMPLE 19

|  | % w/w |
|---|---|
| Sodium lauryl ether sulphate (2EO) | 16.0 |
| Cocoamidopropylbetaine | 2.0 |
| Guar Hydroxypropyltrimonium chloride | 0.1 |
| Dimethicone | 1.0 |
| Curcumin | 1 |
| Benzoic acid | 0.6 |
| Colour | qs |
| Perfume | qs |
| Water | to 100 |

Examples 20 to 23 illustrate hair conditioner compositions according to the invention.

EXAMPLE 20

|  | % w/w |
|---|---|
| Cetyltrimethylammonium chloride | 1.0 |
| $C_{16-18}$ fatty alcohol | 2.4 |
| Paraffin wax | 1.0 |
| Glyceryl monostearate | 1.0 |
| Parsol 1789 | 0.5 |
| Octylmethoxycinnamate | 2.0 |
| Sorbic acid | 0.5 |
| Methyl parabens | 0.2 |
| Propyl parabens | 0.05 |
| Perfume + colour | qs |
| Water | to 100 |

EXAMPLE 21

|  | % w/w |
|---|---|
| Cetyltrimethyl ammonium chloride | 0.7 |
| $C_{16-18}$ fatty alcohol | 2.0 |
| Hydroxyethyl cellulose (Natrosol 250 HR) | 1.0 |
| Stearyl stearate | 0.5 |
| Parsol 1789 | 1.2 |
| $TiO_2$ (ultra fine) | 0.5 |
| Sodium benzoate | 0.5 |
| Perfume, colour | qs |
| Water | to 100 |

EXAMPLE 22

|  | % w/w |
|---|---|
| Cetyltrimethylammonium chloride | 1.0 |
| $C_{16-18}$ fatty alcohol | 2.4 |
| Paraffin wax | 1.0 |
| Glyceryl monostearate | 1.0 |
| Pongamol | 0.5 |
| Parsol MCX | 1.0 |
| Sorbic acid | 0.5 |
| Methyl parabens | 0.2 |
| Perfume + colour | qs |
| Water | to 100 |

EXAMPLE 23

|  | % w/w |
|---|---|
| Cetyltrimethyl ammonium chloride | 1.1 |
| $C_{16-18}$ fatty alcohol | 2.5 |
| Hydroxyethyl cellulose (Natrosol 250 HR) | 0.8 |
| Stearyl stearate | 0.5 |
| Curcumin | 0.5 |
| Octylmethoxycinnamate | 2.0 |
| Dimethicone | 1.0 |
| Sodium salicylate | 0.5 |
| Perfume, colour | qs |
| Water | to 100 |

We claim:

1. A preserved sunscreen composition suitable for topical application to the surface of the human body, in